United States Patent
Fukuda et al.

(10) Patent No.: US 8,309,150 B2
(45) Date of Patent: Nov. 13, 2012

(54) METHOD OF PRODUCING CHLOROGENIC ACID COMPOSITION

(75) Inventors: Masahiro Fukuda, Sumida-ku (JP); Hirokazu Takahashi, Sumida-ku (JP); Atsushi Konishi, Sumida-ku (JP)

(73) Assignee: Kao Corporation, Tokyo (JP)

(*) Notice: Subject to any disclaimer, the term of this patent is extended or adjusted under 35 U.S.C. 154(b) by 367 days.

(21) Appl. No.: 11/815,223

(22) PCT Filed: Feb. 28, 2006

(86) PCT No.: PCT/JP2006/303680
§ 371 (c)(1), (2), (4) Date: Aug. 1, 2007

(87) PCT Pub. No.: WO2006/093114
PCT Pub. Date: Sep. 8, 2006

(65) Prior Publication Data
US 2009/0053381 A1    Feb. 26, 2009

(30) Foreign Application Priority Data
Mar. 1, 2005 (JP) ................................. 2005-055319

(51) Int. Cl.
*A23F 5/24* (2006.01)
(52) U.S. Cl. ......... 426/432; 426/594; 426/427; 426/428
(58) Field of Classification Search .................. 426/427, 426/432, 425, 428, 431, 594
See application file for complete search history.

(56) References Cited

U.S. PATENT DOCUMENTS

| | | | |
|---|---|---|---|
| 4,247,570 A | 1/1981 | Zosel | |
| 2002/0051810 A1 | 5/2002 | Suzuki et al. | |
| 2002/0192317 A1 | 12/2002 | Okawa et al. | |
| 2003/0003212 A1 | 1/2003 | Chien et al. | |
| 2004/0213881 A1 * | 10/2004 | Chien et al. | 426/534 |
| 2004/0266999 A1 * | 12/2004 | Kuriki et al. | 536/8 |

FOREIGN PATENT DOCUMENTS

| | | |
|---|---|---|
| CN | 1398845 A | 2/2003 |
| DE | 196 04 030 A1 | 8/1997 |
| EP | 1 399 034 | 3/2004 |
| JP | 53-18772 | 2/1978 |
| JP | 4-145048 | 5/1992 |
| JP | 4-145049 | 5/1992 |
| JP | 6-142405 | 5/1994 |
| JP | 2002-53464 | 2/2002 |
| JP | 2002-87977 | 3/2002 |
| JP | 2003210119 A * | 3/2003 |
| JP | 2004-528050 | 9/2004 |
| JP | 2005-263632 | 9/2005 |
| WO | WO 02/100192 A1 | 12/2002 |

OTHER PUBLICATIONS

Amberlite XAD-4 Product Data Sheet, Https://www.rohmhaas.com/ionexchange/Pharmaceuticals/Bioprocessing_doc/english/xad4.PDF Oct. 2003.*
JP2003-210119 A, Inami et al., Mar. 2003, Machine Translation pp. 1-6.*
P. Chambel, et al., "Development of an HPLC/Diode-Array Detector Method for Simultaneous Determination of 5-HMF, Furfural, 5-0-Caffeoylquinic Acid and Caffeine in Coffee", Journal of Liquid Chromatography & Related Technologies, vol. 20, No. 18, 1997, pp. 2949 to 2957.
Liu Bin, et al., "Factor Effecting on Absorption Separation of Chemical Component in Herbal Medicine by Macroporous Resin", Chinese Traditional and Herbal Drugs, vol. 33, No. 5, Dec. 31, 2002, pp. 475-476, and partial English translation.
U.S. Appl. No. 12/741,424, filed May 5, 2010, Ogura, et al.

* cited by examiner

*Primary Examiner* — Kelly Bekker
*Assistant Examiner* — Hong T Yoo
(74) *Attorney, Agent, or Firm* — Oblon, Spivak, McClelland, Maier & Neustadt, L.L.P.

(57) ABSTRACT

The present invention provides a method for obtaining a chlorogenic acid composition which contains high concentration of chlorogenic acids and a reduced amount of caffeine at a high yield.

A method of producing a chlorogenic acid composition, which comprises allowing a water-soluble composition extracted from raw coffee beans or roasted coffee beans to be adsorbed to a column filled with an adsorbent and then eluting a chlorogenic acid composition by passing a 0.5 to 20 vol % ethanol aqueous solution.

17 Claims, No Drawings

METHOD OF PRODUCING CHLOROGENIC ACID COMPOSITION

FIELD OF THE INVENTION

The present invention relates to a method of producing a highly purified chlorogenic acid composition.

BACKGROUND OF THE INVENTION

Cardiac diseases, such as stenocardia, myocardial infarction and heart failure, and cerebrovascular diseases, such as cerebral infarction, cerebral hemorrhage and subarachnoid hemorrhage, are correlated closely with high blood pressure. These diseases are the second and third leading cause of death in Japan, respectively. According to the National Livelihood Survey published in 1998 by the Ministry of Health and Welfare, the number of outpatients with hypertension amounts to 64 per 1000 patients, and hypertension ranks first in the etiology surveyed in Japan. Among the therapeutic measures aimed at high-blood pressure are antihypertensives, such as diuretic drugs, sympatholytic drugs, vasodilating drugs and angiotensin converting enzyme inhibitors. These medicaments are applied primarily to severe hypertension patients. On the other hand, general therapeutic methods aimed at improving lifestyle habits, such as diet therapy, exercise therapy, control of drinking and smoking, are acknowledged to be of importance, in that these methods are widely applicable to many hypertension patients ranging from mild hypertension through severe hypertension. Among them, dietary habit is said to be particularly important. And there are traditionally many kinds of food products said to have antihypertensive effects. Searches for antihypertensive materials derived from food have been conducted actively heretofore, and a number of active substances having such effects have been isolated and identified.

Chlorogenic acids, which are contained about 6 to 9% in a raw coffee bean, have an excellent antihypertensive effect (Patent Documents 1 and 2). Nonetheless, because caffeine is also contained normally 1 to 4% in a raw coffee bean, it is said that the excessive intake of such ingredients could cause adverse effects at the same time, such as hypersensitivity, nausea and sleeplessness. On this account, a method capable of selectively removing caffeine from a chlorogenic acid composition containing caffeine has been investigated.

So far, there have been some reports associated with decaffeinating methods, for example, a method of contacting coffee with a caffeine adsorbent such as activated carbon under 120 to 250 atm (Patent Document 3) and a method of contacting an aqueous solution containing caffeine with activated clay or acid clay to thereby selectively remove caffeine (Patent Document 4).

However, the former method relates to a supercritical extraction technology, and its process requires a great deal of facilities, so that this method lacks simplicity in terms of industrial operation. Furthermore, there is another problem in that this method brings a detrimental change to the composition of chlorogenic acids serving as active ingredients, without contributing to the selective removal of only caffeine. On the other hand, the latter method can selectively remove caffeine simply by use of activated clay or acid clay, but this method raised the problem that the recovery ratio of chlorogenic acids does not suffice.

In addition, a method characterized by performing extraction from raw coffee beans with an aqueous solvent, adsorbing chlorogenic acids with a synthesized adsorbent, and treating it with a dilute alkali to selectively obtain chlorogenic acids (Patent Document 5), and a method characterized by performing a treatment in contact with a strong-acid cation exchange resin to selectively obtain chlorogenic acids (Patent Document 6) can be mentioned. Nonetheless, these methods require cumbersome ion exchange treatments.

[Patent document 1]: JP-A-2002-53464
[Patent document 2]: JP-A-2002-87977
[Patent document 3]: JP-A-53-18772
[Patent document 4]: JP-A-06-142405
[Patent document 5]: JP-A-04-145049
[Patent document 6]: JP-A-04-145048

DISCLOSURE OF THE INVENTION

The present invention is related to a method of producing a chlorogenic acid composition, which includes allowing a water-soluble composition extracted from raw coffee beans or roasted coffee beans to be adsorbed to a column filled with an adsorbent and then eluting a chlorogenic acid composition by passing a 0.5 to 20 vol % ethanol aqueous solution.

DETAILED DESCRIPTION OF THE INVENTION

The present invention provides a method of producing a chlorogenic acid composition which contains high concentration of chlorogenic acids having antihypertensive activity and a reduced amount of caffeine at a high yield.

The present inventors have found that a chlorogenic acid composition containing a reduced amount of caffeine can be readily obtained by allowing an extracted solution of raw coffee beans or the like to be adsorbed to a column filled with an adsorbent and then eluting a chlorogenic acid composition with a low concentration ethanol aqueous solution.

According to the present invention, caffeine can be reduced more effectively, and a chlorogenic acid composition with a higher purity can be obtained in a higher yield at a lower cost, than any conventional method of producing chlorogenic acid compositions.

The water-soluble composition extracted from raw coffee beans or roasted coffee beans in the present invention contains (A) monocaffeoylquinic acid ingredient, (B) ferulaquinic acid ingredient and (C) dicaffeoylquinic acid ingredient. Ingredient (A) includes 3-caffeoylquinic acid, 4-caffeoylquinic acid and 5-caffeoylquinic acid. Ingredient (B) includes 3-ferulaquinic acid, 4-ferulaquinic acid and 5-ferulaquinic acid. Ingredient (C) includes 3,4-dicaffeoylquinic acid, 3,5-dicaffeoylquinic acid and 4,5-dicaffeoylquinic acid.

The above water-soluble composition to be used in the present invention can be obtained by extracting from raw coffee beans or roasted coffee beans and/or ground product thereof with water, which may be either cold water or hot water, by a conventional method in the art. The temperature of water is preferably 70° C. to boiling temperature at the time of performing the extraction from raw coffee beans or roasted coffee beans, from the viewpoint of increasing extraction efficiency of chlorogenic acids, and more preferably 80° C. to boiling temperature. The amount of water when extracting from raw coffee beans or roasted coffee beans is preferably 5 to 60 times by mass, more preferably 5 to 40 times by mass of that of the raw coffee beans or roasted coffee beans. The extraction time from raw coffee beans or roasted coffee beans is preferably 10 to 120 minutes, more preferably 20 to 90 minutes, and far more preferably 30 to 60 minutes. When the extraction time is too short, elution of chlorogenic acids is insufficient whereas bad smell becomes strong when the extraction time is too long.

The kind of raw coffee beans or roasted coffee beans to be used in the present invention is not limited in particular, but, for example, includes Brazilian, Colombian, Tanzanian and Mocha. The kind of beans includes Arabica coffee and Robusta coffee. Either one kind of coffee beans or blends of plural kinds may be used.

As for the above raw coffee beans, dry beans can be used and as for the roasted coffee beans those obtained by ordinary roasting methods can be used. Since the chlorogenic acid content generally decreases as the roast degree of the beans becomes deeper, light roasting not less than 25 in terms of L value is preferable, the L value of 30 or more is even preferable and the L value of 35 to 40 is far preferable.

The adsorbent to be used in the present invention is preferably a hydrophobic adsorbent, and a synthesized adsorbent such as a styrene-type synthesized adsorbent such as styrene-divinylbenzene, modified styrene-divinylbenzene and a methyl methacrylate-type synthesized adsorbent are more preferable. Examples of the styrene-divinylbenzene-type synthesized adsorbents include, as for trade names, Diaion HP-20, HP-21, Sepabeads SP70, SP700, SP825, and SP-825 manufactured by Mitsubishi Chemical Corp., Amberlite XAD4, XAD16HP, XAD1180, and XAD2000 from Organo Corp. (available from Rohm and Haas Co., U.S.), Duolite S874, S876 from Sumitomo Chemical Co., Ltd. (available from Rohm and Haas Co., U.S.).

Examples of the modified styrene-divinylbenzene-type synthesized adsorbents in which adsorbing power is enhanced by nucleus substitution with a bromine atom include, as for trade names, Sepabeads SP205, SP206, and SP207 manufactured by Mitsubishi Chemical Corp. The modified styrene-divinylbenzene-type synthesized adsorbents are preferable because they have higher adsorption capacity as compared with unmodified synthesized adsorbents and have high density, which enables upflow extraction in purification process.

Examples of the methacrylate-type synthesized adsorbents include Sepabeads HP1MG, HP2MG manufactured by Mitsubishi Chemical Corp., XAD7HP of Organo Corp. and Duolite S877 of Sumitomo Chemical Co., Ltd. The methyl methacrylate-type synthesized adsorbents have less adsorption amount but they are advantageous in the adsorption of highly polar organic substances.

In the present invention, an aqueous composition extracted from raw coffee beans or roasted coffee beans, for example, an extract of raw coffee beans or roasted coffee beans is passed through a column filled with an adsorbent at first but it is preferable to perform washing beforehand with 95 vol % ethanol aqueous solution under the liquid passing condition of SV (space velocity)=1 to 5 $[h^{-1}]$ and liquid passing factor of 2 to 5 [v/v] for the filling volume of the adsorbent to remove raw material monomers of the adsorbent and impurities in the raw material monomers. Then, the adsorbent is washed with water under the liquid passing condition of SV (space velocity)=1 to 5 $[h^{-1}]$ and liquid passing factor of 1 to 5 [v/v] for the filling volume of the adsorbent to remove ethanol and substitute the contained liquid in the adsorbent with a water-based one, by which adsorption ability of chlorogenic acids is improved.

Furthermore, it is preferable to add a substance having a salting-out effect such as dietary salt to the extract of raw coffee beans or roasted coffee beans to improve adsorption retentivity of chlorogenic acids to the adsorbent. Substances having a salting-out effect include dietary salt (sodium chloride), potassium chloride, magnesium chloride, sodium hydrogensulfite, potassium hydrogensulfite, ammonium sulfate. The substances having a salting-out effect are preferably added in a ratio of 1 to 50 masse, more preferably 10 to 40 mass %, and even more preferably 20 to 30 masse for the raw coffee beans or roasted coffee beans (in terms of raw beans). This is because the dietary salt may remain when the addition amount exceeds 50 masse, which is not preferable in respect of taste.

As for the condition to make an extract of raw coffee beans or roasted coffee beans to pass through the column filled with an adsorbent, the liquid passing factor is preferably 0.5 to 20 [v/v] for the filling volume of the adsorbent, more preferably 0.5 to 10 [v/v], and far more preferably 1 to 8 [v/v]. As for the liquid passing rate, SV (space velocity) is preferably 0.5 to 10 $[h^1]$ and more preferable SV=1 to 5 $[h^1]$.

Furthermore, washing with water with a liquid passing factor of 0.1 to 2.0 [v/v] for the filling volume of the adsorbent is preferably performed after the extract of raw coffee beans or roasted coffee beans is adsorbed to the adsorbent and before an ethanol aqueous solution, which is an eluting liquid, is made to pass. Particularly, when a substance having a salting-out effect is added to enhance adsorption retentivity of chlorogenic acids to the adsorbent, washing with water is effective from the purpose of removing the remaining substance which has a salting-out effect.

As for the condition to desorb the chlorogenic acids with an ethanol aqueous solution after adsorption to the column, a liquid passing rate of 0.5 to 20 vol % of the ethanol aqueous solution is preferable, because the condition facilitates caffeine to be retained in the adsorbent and enables to desorb and purify the chlorogenic acids effectively. Furthermore, the concentration of the ethanol aqueous solution is preferably 1 to 10 vol % and more preferably 2 to 8 vol % in that caffeine can be further reduced. The reason why the concentration for desorption is 0.5 vol % or more is that, when desorption is performed with water or an ethanol aqueous solution of 5% or less, the liquid passing factor to the adsorbent exceeds 10, which needs a large quantity of eluting liquid and lowers the recovery rate of chlorogenic acids to some extent. On the other hand, when caffeine is eluted with an ethanol aqueous solution more than 20 vol %, separation between caffeine and chlorogenic acids is deteriorated.

The liquid passing amount of the ethanol aqueous solution is preferably 0.5 to 10 [v/v], more preferably 1 to 6 [v/v] for the filling volume of the adsorbent. The liquid passing rate of the ethanol aqueous solution is preferably SV (space velocity)=0.5 to 10 $(h^{-1})$, more preferably 2 to 8 $(h^{-1})$.

The adsorbent used in the present invention can be reused by applying a predetermined method after the purification process. Specifically, 90 to 99.5 vol % ethanol aqueous solution is made to pass so that the aqueous solution composition ingredients which remain on the adsorbent and are mainly composed of caffeine are entirely desorbed.

In the chlorogenic acid composition obtained by the present invention, bitterness can be reduced by decreasing caffeine to such a degree that the mass ratio symbolized by "(D)/((A)+(B)+(C))" becomes less than 1/10 wherein (A) is monocaffeoylquinic acid ingredient, (B) is ferulaquinic acid ingredient, (C) is dicaffeoylquinic acid ingredient and (D) is caffeine, and by decreasing the dicaffeoylquinic acid ingredient to such a degree that the mass ratio of a chlorogenic acid composition symbolized by "((A)+(B))/((A)+(B)+(C))" becomes 0.85 or more. In addition, the recovery ratio of chlorogenic acids can be 70 masse or more for the chlorogenic acids in the raw bean extract by the present invention.

The chlorogenic acid composition obtained by the present invention may be used as it is or ethanol may be removed therefrom by methods such as vacuum concentration and membrane concentration. When the composition is used for blending in beverage, it is usually preferable to completely remove ethanol. When powder is desirable as a product form of the chlorogenic acid composition, the composition can be made into powder by methods such as spray drying or freeze-drying. In this case, bad smell derived from raw beans can also be reduced at the same time.

In addition, the chlorogenic acid composition obtained by the production method of the present invention can be subjected to deodorization treatment with activated carbon so that bad smell derived from raw coffee beans can be removed. The activated carbon to be used is not particularly limited as long as it is usable at an industrial level, and commercially available products such as ZN-50 (manufactured by Hokuetsu Carbon Industry), Kuraraycoal GLC, Kuraraycoal PK-D, and Kuraraycoal PW-D (manufactured by Kuraray Chemical Corp.), Shirasagi AW50, Shirasagi A, Shirasagi M, and Shirasagi C (manufactured by Takeda Chemical Industries Corp.) can be used. The pore volume of the activated carbon is preferably 0.01 to 0.8 mL/g and more preferably 0.1 to 0.7 mL/g. As for the specific surface area, those in a range of 800 to 1300 $m^2$/g are preferable, and those in a range of 900 to 1200 $m^2$/g are far preferable. These property values are values based on nitrogen adsorption method.

The activated carbon is added to 100 mass parts of a solution of the chlorogenic acid composition of the present invention preferably in an amount of 0.5 to 5 mass parts, more preferably in an amount of 0.5 to 3 mass parts. When the addition amount of the activated carbon is too little, deodorization effects are not enough and when it is too much, the chlorogenic acid composition is adsorbed by the active carbon and therefore it is not preferable.

The chlorogenic acid composition obtained by the present invention can be blended in container-packed beverage. Usable containers can be provided as normal forms such as molded containers mainly composed of polyethylene terephthalate (so-called PET bottles), metallic cans, paper container composite with metal foils or plastic films and bottles used for ordinary beverage. The container-packed beverage as used herein means beverage drinkable without dilution.

The container-packed beverage mentioned above can be produced, for example, under sterilization conditions prescribed in the food hygiene law when using a container such as metallic can, which can be heat-sterilized after it is filled. As for containers which cannot be retort-sterilized such as PET bottles and paper containers, sterilization conditions equivalent to the above conditions can be applied beforehand, for example, by a method in which the beverage is sterilized at a high temperature in a short time with plate type heat exchangers, then cooled to a certain temperature and filled into the container. The contents of the filled containers may also be blended with other ingredients under sterile condition before packing.

The container-packed beverages blended with a chlorogenic acid composition obtained by the present invention include coffee drinks, tea-type drinks, juice drinks added with fruit juice or vegetables juice, carbonated refreshing drinks.

EXAMPLES

Method of Measuring Chlorogenic Acids and Caffeine

A drink filtrated with a filter (0.8 μm), diluted with distilled water and filled in a container was subjected to a gradient method using a high performance liquid chromatograph (model SCL-10AVP) manufactured by Shimazu Corp. equipped with an octadecyl group introduced packed column for liquid chromatograph, L-column TM ODS (4.6 mm φ×250 mm: manufactured by Incorporated Foundation, Chemicals Evaluation and Research Institute) at a column temperature of 35° C. and a flow rate of 1 mL/min. Mobile phase A liquid was a distilled water containing 0.1 mol/L acetic acid and B liquid was an acetonitrile solution containing 0.1 mol/L acetic acid, 20 μL sample was injected and UV detector wavelength was 280 nm.

Example 1

100 g of robusta raw beans made in Indonesia were minced, extracted with 2000 g of deionized water at 95° C. for 30 minutes, cooled, squeezed, centrifugally separated and filtrated with a wire netting and #2 filter paper to obtain 1530 g of extract. The concentration of chlorogenic acids in the extract was 369.0 mg/100 mL and 5.65 g of chlorogenic acids were contained. The total concentration of monocaffeoylquinic acid and ferulaquinic acid of that was 284.1 mg/100 mL and 4.35 g. The concentration of caffeine was 101.1 mg/100 mL, 1.55 g of caffeine was contained, and a ratio of caffeine/chlorogenic acids was 0.274 (−). Then, 30 g of dietary salt was added in order to enhance adsorption retentivity.

252.4 mL of synthesized adsorbent, Sepabeads SP-207 (manufactured by Mitsubishi Chemical Corp.) filled in a stainless steel column (inside diameter 33 mm×300 mm in height, 292 mL in volume) was washed with 1262 mL of 95% (v/v) ethanol (5 times volume of the synthesized adsorbent) at SV=7.8 ($h^{-1}$) beforehand, and then washed with 1136 mL of water (4.5 times volume of the synthesized adsorbent) at SV=5.2 ($h^{-1}$).

Total amount of the obtained extract (6 times volume of the synthesized adsorbent) was made to pass at SV=5.2 ($h^1$). The liquid which passed through the column did not contain chlorogenic acids and almost all chlorogenic acids were adsorbed by the synthesized adsorbent.

Subsequently, the column was washed with 126.2 mL of water (0.5 times volume of the synthesized adsorbent) at SV=5.2 ($h^{-1}$). The washing water contained 5.3 mg/100 mL of chlorogenic acids, and there was a little elution of chlorogenic acids by the washing with water. In addition, it was not at all salty when tasting evaluation was performed after the washing with water.

After washing with water, 1262 mL of 5% (v/v) ethanol aqueous solution (5 times volume of the synthesized adsorbent) was made to pass at SV=5.2 ($h^{-1}$). 1,251 mL of the eluate was collected, and ethanol was removed by vacuum concentration; and 20.0 g of chlorogenic acid composition of the present invention was obtained.

This concentrate contained 4.53 g of chlorogenic acids and the total amount of monocaffeoylquinic acid and ferulaquinic acids was 4.12 g and the mass ratio of monocaffeoylquinic acid and ferulaquinic acid in the chlorogenic acids was 91.0%. Recovery ratio of chlorogenic acids from the raw bean extract was 80.1%, and no caffeine was contained.

Example 2

The extract obtained by the same operation as in Example 1 was made to pass the synthesized adsorbent and the chlorogenic acid composition of the present invention was obtained by performing a similar operation except that 505 mL (2 times volume of the synthesized adsorbent) of 10% (v/v) ethanol aqueous solution was made to pass at SV=5.2 ($h^{-1}$).

The concentrate contained 4.99 g of chlorogenic acids and the total amount of monocaffeoylquinic acid and ferulaquinic acids was 4.35 g and the mass ratio of monocaffeoylquinic acid and ferulaquinic acid in the chlorogenic acids was 87.2%. Recovery ratio of chlorogenic acids from the raw bean extract was 88.3%, 0.07 g of caffeine was contained and caffeine/chlorogenic acids was 0.014 (−).

Example 3

The extract obtained by the same operation as in Example 1 was made to pass the synthesized adsorbent and the chlorogenic acid composition of the present invention was obtained by performing a similar operation except that 505 mL (2 times volume of the synthesized adsorbent) of 20% (v/v) ethanol aqueous solution was made to pass at SV=5.2 ($h^{-1}$).

The concentrate contained 5.13 g of chlorogenic acids and the total amount of monocaffeoylquinic acid and ferulaquinic acids was 4.40 g and the mass ratio of monocaffeoylquinic acid and ferulaquinic acid in the chlorogenic acids was 85.8%. Recovery ratio of chlorogenic acids from the raw bean extract was 90.8%, 0.2 g of caffeine was contained and caffeine/chlorogenic acids was 0.039 (−).

Example 4

The same extraction operation as in Example 1 was performed except that robusta beans made in Indonesia roasted to 35 in terms of L value were used and the extract of the roasted beans contained 5.04 g of chlorogenic acids and the total amount of monocaffeoylquinic acid and ferulaquinic acids was 3.93 g. 1.65 g of caffeine was also contained and the ratio of caffeine/chlorogenic acids was 0.327 (−).

Further, the operation which was totally the same as in Example 1 was performed and chlorogenic acid composition of the present invention was obtained. The concentrate contained 3.69 g of chlorogenic acids and the mass ratio of monocaffeoylquinic acid in the chlorogenic acids was 86.5%. Recovery ratio of chlorogenic acids from the roasted bean extract was 76.5%, no caffeine was contained and caffeine/chlorogenic acids was 0.0 (−).

Example 5

504.8 mL of a synthesized adsorbent Sepabeads SP-207 (manufactured by Mitsubishi Chemical Corp.) filled in a stainless steel column (inside diameter 33 mm×300 mm in height, 584 mL in volume) was washed with 2524 mL of 95% (v/v) ethanol (5 times volume of the synthesized adsorbent) at SV=7.8 ($h^{1}$) beforehand, and then washed with 2272 mL of water (4.5 times volume of the synthesized adsorbent) at SV=5.2 ($h^{-1}$).

The same extract as in Example 4 was used and the total amount of obtained extract (3 times volume of the synthesized adsorbent) was made to pass at SV=3.2 ($h^{-1}$). Subsequently, the column was washed with 504.8 mL of water (1.0 times volume of the synthesized adsorbent) at SV=3.2 ($h^{-1}$). The washing water contained 3.5 mg/100 mL of chlorogenic acids, and there was a little elution of chlorogenic acids by the washing with water.

After washing with water, 5048 mL of 5% (v/v) ethanol aqueous solution (10 times volume of the synthesized adsorbent) was made to pass at SV=3.2 ($h^{-1}$). 1251 mL of the eluate was collected, and ethanol was removed by vacuum concentration; and 22.0 g of chlorogenic acid composition of the present invention was obtained. The concentrate contained 4.32 g of chlorogenic acids and the mass ratio of monocaffeoylquinic acid and ferulaquinic acid in the chlorogenic acids was 89.2%. Recovery ratio of chlorogenic acids from the roasted bean extract was 85.8%, no caffeine was contained and caffeine/chlorogenic acids was 0.0 (−).

Comparative Example 1

The same extraction operation as in Example 1 was performed and a chlorogenic acid composition was obtained by performing a similar operation except that 5048 mL (20 times volume of the synthesized adsorbent) of water was made to pass at SV=5.2 ($h^{-1}$).

Comparative Example 2

The same extraction operation as in Example 1 was performed and a chlorogenic acid composition was obtained by performing a similar operation except that 1265.8 mL times volume of the synthesized adsorbent) of 5 mass % sodium bicarbonate aqueous solution was made to pass at SV=5.2 ($h^{-1}$).

Comparative Example 3

The same extraction operation as in Example 1 was performed and a chlorogenic acid composition was obtained by performing a similar operation except that 505 mL (2 times volume of the synthesized adsorbent) of 40 vol % of ethanol aqueous solution was made to pass at SV=5.2 ($h^{-1}$).

The results of the analysis are shown in Table 1.

TABLE 1

<Analytical values after treatment with synthesized adsorbent>

|  |  | Example 1 | Example 2 | Example 3 | Example 4 | Example 5 | Comparative Example 1 | Comparative Example 2 | Comparative Example 3 |
|---|---|---|---|---|---|---|---|---|---|
| Type of coffee beans |  | Raw beans | Raw beans | Raw beans | Roasted beans | Roasted beans | Raw beans | Raw beans | Raw beans |
| Type of synthesized adsorbent |  | SP-207 | SP-207 | SP-207 | SP-207 | SP-207 | SP-207 | SP-207 | SP-207 |
| Eluting liquid |  | Ethanol | Ethanol | Ethanol | Ethanol | Ethanol | Water | 5 mass % sodium bicarbonate aqueous solution | Ethanol |
| Concentration of ethanol aqueous solution | [% v/v] | 5 | 10 | 20 | 5 | 5 | 0 | 0 | 40 |
| Ratio of eluting liquid to synthesized adsorbent | [Volume ratio] | 5 | 2 | 2 | 5 | 10 | 20 | 5 | 2 |
| Chlorogenic acids content | [g] | 4.53 | 4.99 | 5.13 | 3.69 | 4.32 | 4.00 | 1.98 | 5.15 |

TABLE 1-continued

<Analytical values after treatment with synthesized adsorbent>

|  |  | Example 1 | Example 2 | Example 3 | Example 4 | Example 5 | Comparative Example 1 | Comparative Example 2 | Comparative Example 3 |
|---|---|---|---|---|---|---|---|---|---|
| Content of monocaffeoylquinic acid and ferulaquinic acidt | [g] | 4.12 | 4.35 | 4.40 | 3.19 | 3.86 | 3.32 | 1.59 | 4.15 |
| Content ratio of monocaffeoylquinic acid and ferulaquinic acid | [%] | 91.0 | 87.2 | 85.8 | 86.5 | 89.2 | 83.1 | 80.1 | 80.6 |
| Caffeine content | [g] | 0 | 0.07 | 0.20 | 0 | 0 | 0 | 0 | 0.98 |
| Ratio of caffeine/chlorogenic acids | [-] | 0 | 0.014 | 0.039 | 0 | 0 | 0 | 0 | 0.190 |
| Recovery ratio of chlorogenic acids | [Mass %] | 80.1 | 88.3 | 90.8 | 76.5 | 85.8 | 65.8 | 35.0 | 91.1 |

<Analytical Values of Raw Bean Extract>
Concentration of chlorogenic acids: 369.0 mg/100 mL,
Content of chlorogenic acids: 5.65 g,
Concentration of monocaffeoylquinic acid+ferulaquinic acid: 284.1 mg/100 mL,
Content of monocaffeoylquinic acid+ferulaquinic acid: 4.35 g,
Concentration of caffeine: 101.1 mg/100 mL,
Content of caffeine: 1.55 g,
Ratio of caffeine/chlorogenic acids: 0.274(−)
<Analytical Values of Roasted Bean Extract>
Concentration of chlorogenic acids: 344.0 mg/100 mL,
Content of chlorogenic acids: 5.04 g,
Concentration of monocaffeoylquinic acid+ferulaquinic acid: 268.2 mg/100 mL,
Content of monocaffeoylquinic acid+ferulaquinic acid: 3.93 g,
Concentration of caffeine: 118.0 mg/100 mL,
Content of caffeine: 1.65 g,
Ratio of caffeine/chlorogenic acids: 0.327(−)

According to the method of the present invention, before and after the treatment, highly purified chlorogenic acid compositions having reduced caffeine content can be obtained in a high recovery ratio.

The invention claimed is:

1. A method of producing a chlorogenic acid composition, said method comprising:
    allowing a water-soluble composition that contains monocaffeoylquinic acid, ferulaquinic acid and dicaffeoylquinic acid and that is extracted from raw coffee beans or roasted coffee beans to be adsorbed to a column filled with an adsorbent selected from the group consisting of styrene-divinylbenzene, modified styrene-divinylbenzene and methyl methacrylate type adsorbents; and then
    eluting a chlorogenic acid composition adsorbed on the column by passing a 0.5 to 10 vol % ethanol aqueous solution;
    wherein the extraction from the raw coffee beans or roasted coffee beans is performed for 10 to 120 minutes with water at a temperature of from 70° C. to boiling; and
    wherein the mass ratio of the chlorogenic acid composition denoted by ((A)+(B))/((A)+(B)+(C)) is 0.85 or more, wherein (A) is monocaffeoylquinic acid, (B) is ferulaquinic acid and (C) is dicaffeoylquinic acid; and
    the mass ratio of caffeine in the chlorogenic acid composition denoted by (D)/((A)+(B)+(C)) is 0.014 or less, wherein (A) is monocaffeoylquinic acid, (B) is ferulaquinic acid, (C) is dicaffeoylquinic acid and (D) is caffeine.

2. The method according to claim 1, wherein a passing rate in terms of space velocity of the ethanol aqueous solution is 0.5 to 10 $h^{-1}$.

3. The method according to claim 1, wherein the column is washed with water in an amount of 0.5 to 2.0 times more volume than the volume of adsorbent before the passing of the ethanol aqueous solution in the column.

4. The method according to claim 1, which comprises adding a substance having a salting-out effect to the water-soluble composition extracted from raw coffee beans or roasted coffee beans in an amount of 10 to 40 by mass % of the total weight of the raw coffee beans or roasted coffee beans.

5. The method according to claim 1, wherein the recovery ratio of chlorogenic acids is 70 mass % or more to chlorogenic acids in a water-soluble composition extracted from the raw coffee beans or roasted coffee beans.

6. The method according to claim 1, wherein the monocaffeoylquinic acid (A) comprises at least one of 3-caffeoylquinic acid, 4-caffeoylquinic acid, and 5-caffeoylquinic acid.

7. The method according to claim 1, wherein the ferulaquinic acid (B) comprises at least one of 3-ferulaquinic acid, 4-ferulaquinic acid, and 5-ferulaquinic acid.

8. The method according to claim 1, wherein the dicaffeoylquinic acid (C) comprises at least one of 3,4-dicaffeoylquinic acid, 3,5-dicaffeoylquinic acid, and 4,5-dicaffeoylquinic acid.

9. The method according to claim 1, wherein said eluting step comprises passing 1 to 8 vol % of the ethanol aqueous solution.

10. The method according to claim 1, wherein a passing rate in terms of space velocity of the ethanol aqueous solution is 2 to 8 $h^{-1}$.

11. The method according to claim 1, wherein the extraction from raw the coffee beans or roasted coffee beans is performed with water at a temperature of from 80° C. to boiling.

12. The method according to claim 1, wherein the extraction from raw the coffee beans or roasted coffee beans is performed for 20 to 90 minutes.

13. The method according to claim 1, wherein the extraction from raw the coffee beans or roasted coffee beans is performed for 30 to 60 minutes.

14. The method according to claim 1, wherein said styrene-divinylbenzene adsorbent is a brominated styrene-divinylbenzene.

15. A method for selectively removing caffeine from an aqueous coffee solution containing chlorogenic acids and caffeine comprising:
    extracting raw or roasted raw coffee beans with water to produce an aqueous solution containing chlorogenic acids and caffeine;

contacting the aqueous solution with an adsorbent that binds to caffeine and to chlorogenic acids in the aqueous solution, but that retains bound caffeine and releases chlorogenic acid when contacted with an aqueous alcohol solution containing 0.5 vol. % to 10 vol. % ethanol;

contacting the adsorbent that has bound caffeine and chlorogenic acid with an aqueous alcohol solution containing 0.5% to 10 vol. % ethanol to elute chlorogenic acids, and recovering the eluted chlorogenic acids;

wherein the eluted chlorogenic acids have a lower mass ratio of caffeine to chlorogenic acid than that of the original aqueous coffee solution; and wherein the mass ratio of caffeine in the eluted chlorogenic acid composition denoted (D)/((A)+(B)+(C)) is 0.014 or less wherein (A) is monocaffeoylquinic acid, (B) is ferulaquinic acid, (C) is dicaffeoylquinic acid and (D) is caffeine; wherein the adsorbent is selected from the group consisting of styrene-divinylbenzene, modified styrene-divinylbenzene and methyl methacrylate type adsorbent.

16. The method of claim 15, wherein the mass ratio of the chlorogenic acid composition recovered is denoted by ((A)+(B))/((A)+(B)+(C)) is 0.85 or more, wherein (A) is monocaffeoylquinic acid, (B) is ferulaquinic acid and (C) is dicaffeoylquinic acid.

17. The method of claim 15, wherein 1 to 50 mass % of a substance having a salting out effect selected from the group consisting of sodium chloride, potassium chloride, magnesium chloride, sodium hydrogensulfite, potassium hydrogen sulfite, based on total weight of the raw coffee beans or roasted coffee beans and ammonium sulfate is added to the extract of raw of the roasted coffee beans.

* * * * *

UNITED STATES PATENT AND TRADEMARK OFFICE
CERTIFICATE OF CORRECTION

PATENT NO. : 8,309,150 B2
APPLICATION NO. : 11/815223
DATED : November 13, 2012
INVENTOR(S) : Masahiro Fukuda et al.

It is certified that error appears in the above-identified patent and that said Letters Patent is hereby corrected as shown below:

Delete the text of Claim 11 at Column 10, line 50 in it's entirety and replace with the following:

-- tion from the raw coffee beans or roasted coffee beans is --

Delete the text of Claim 12 at Column 10, line 54 in it's entirety and replace with the following:

-- tion from the raw coffee beans or roasted coffee beans is --

Delete the text of Claim 17 at Column 12, lines 10-16 in it's entirety and replace with the following:

-- 17. The method of claim 15, wherein 1 to 50 mass % of a substance having a salting out effect selected from the group consisting of sodium chloride, potassium chloride, magnesium chloride, sodium hydrogensulfite, potassium hydrogen sulfite, and ammonium sulfate based on total weight of the raw coffee beans or roasted coffee beans is added to the extract of the raw coffee beans or roasted coffee beans --

Signed and Sealed this
Twelfth Day of March, 2013

Teresa Stanek Rea
*Acting Director of the United States Patent and Trademark Office*